US009320662B2

(12) United States Patent
Hayes et al.

(10) Patent No.: US 9,320,662 B2
(45) Date of Patent: Apr. 26, 2016

(54) PATIENT SUPPORT APPARATUS WITH IN-ROOM DEVICE COMMUNICATION

(75) Inventors: Michael Joseph Hayes, Kalamazoo, MI (US); Aaron Douglas Furman, Kalamazoo, MI (US); Joshua Elmer Mix, Portage, MI (US); Richard A. Derenne, Portage, MI (US); John P. Geer, Ann Arbor, MI (US)

(73) Assignee: Stryker Corporation, Kalamazoo, MI (US)

( * ) Notice: Subject to any disclaimer, the term of this patent is extended or adjusted under 35 U.S.C. 154(b) by 80 days.

(21) Appl. No.: 13/570,934

(22) Filed: Aug. 9, 2012

(65) Prior Publication Data

US 2013/0091631 A1  Apr. 18, 2013

Related U.S. Application Data

(60) Provisional application No. 61/548,491, filed on Oct. 18, 2011.

(51) Int. Cl.
*A61G 7/002* (2006.01)
*A61G 7/018* (2006.01)

(52) U.S. Cl.
CPC .............. *A61G 7/002* (2013.01); *A61G 7/018* (2013.01); *A61G 2203/20* (2013.01); *A61G 2203/22* (2013.01); *A61G 2205/60* (2013.01)

(58) Field of Classification Search
CPC ... A61G 7/002; A61G 7/018; A61G 2203/20; A61G 2205/60; A61G 2203/22
USPC ........... 5/600, 616; 340/10.1, 539.11, 539.12, 340/573.1
See application file for complete search history.

(56) References Cited

U.S. PATENT DOCUMENTS

| 5,781,442 | A  | * | 7/1998  | Engleson et al. ............ 700/214 |
|-----------|----|---|---------|-------------------------------------|
| 6,021,533 | A  | * | 2/2000  | Ellis et al. ......................... 5/600 |
| 6,147,592 | A  | * | 11/2000 | Ulrich et al. ............. 340/286.07 |
| 6,160,478 | A  | * | 12/2000 | Jacobsen et al. ......... 340/539.12 |
| 6,208,250 | B1 | * | 3/2001  | Dixon et al. ............... 340/573.1 |
| 6,236,317 | B1 | * | 5/2001  | Cohen et al. ............... 340/573.1 |
| 6,727,818 | B1 | * | 4/2004  | Wildman et al. .......... 340/573.1 |
| 6,791,460 | B2 | * | 9/2004  | Dixon et al. ............... 340/573.1 |
| 6,822,571 | B2 | * | 11/2004 | Conway ..................... 340/573.1 |
| 6,954,148 | B2 | * | 10/2005 | Pulkkinen et al. ......... 340/572.1 |
| 7,014,000 | B2 | * | 3/2006  | Kummer et al. ............. 180/19.3 |
| 7,015,816 | B2 | * | 3/2006  | Wildman et al. .......... 340/573.1 |
| 7,154,397 | B2 | * | 12/2006 | Zerhusen et al. .......... 340/573.1 |

(Continued)

*Primary Examiner* — David E Sosnowski
*Assistant Examiner* — Eric Kurilla
(74) *Attorney, Agent, or Firm* — Warner Norcross & Judd LLP (57) ABSTRACT

A patient support system includes a patient support apparatus—which may be a bed or the like—and one or more mobile electronic tags that are positionable in the room and which communicate wirelessly with the patient support apparatus. The electronic tags are attached to one or more of a patient, a medical device, or a caregiver. After detecting the tag(s), the patient support apparatus implements one or more patient care protocols, and provides alerts if the protocols are violated. The implementation may be automatic or require caregiver confirmation. The protocols can be for fall prevention, bed sore prevention, pneumonia prevention, caregiver hand washing, dialysis, and/or other purposes. The patient support apparatus determines the protocol(s) based on one or more of the following: the type of medical device, the specific patient, the presence or absence of the caregiver, and/or information transmitted to, or input into, the patient support apparatus.

15 Claims, 4 Drawing Sheets

(56) References Cited

U.S. PATENT DOCUMENTS

| | | |
|---|---|---|
| 7,408,470 B2 | 8/2008 | Wildman et al. |
| 7,450,024 B2* | 11/2008 | Wildman et al. ............ 340/669 |
| 7,551,092 B1* | 6/2009 | Henry ....................... 340/573.1 |
| 7,598,853 B2 | 10/2009 | Becker et al. |
| 7,682,464 B2* | 3/2010 | Glenn et al. ................ 134/56 R |
| 7,690,059 B2 | 4/2010 | Lemire et al. |
| 7,702,481 B2 | 4/2010 | Dionne et al. |
| 7,770,782 B2* | 8/2010 | Sahud .......................... 235/375 |
| 7,812,730 B2 | 10/2010 | Wildman et al. |
| 7,898,407 B2* | 3/2011 | Hufton et al. ........... 340/539.11 |
| 7,911,349 B2* | 3/2011 | Zerhusen et al. ......... 340/573.1 |
| 7,936,275 B2* | 5/2011 | Bolling ..................... 340/573.1 |
| 7,986,227 B2* | 7/2011 | Yankelevitz et al. .... 340/539.12 |
| 7,987,069 B2* | 7/2011 | Rodgers et al. ............. 702/150 |
| 8,011,039 B2* | 9/2011 | Stryker et al. .................... 5/600 |
| 8,196,810 B2* | 6/2012 | Sahud .......................... 235/375 |
| 8,319,633 B2* | 11/2012 | Becker et al. ........... 340/539.12 |
| 8,395,515 B2* | 3/2013 | Tokhtuev et al. ............. 340/603 |
| 8,437,876 B2* | 5/2013 | Receveur et al. ............ 700/275 |
| 8,461,968 B2* | 6/2013 | Ball et al. ................. 340/286.02 |
| 8,461,982 B2* | 6/2013 | Becker et al. ........... 340/539.12 |
| 8,502,681 B2* | 8/2013 | Bolling et al. ............ 340/573.1 |
| 8,525,666 B2* | 9/2013 | Melker et al. ........... 340/539.11 |
| 8,701,229 B2* | 4/2014 | Lemire et al. .................... 5/510 |
| 8,707,483 B2* | 4/2014 | Richards et al. ................. 5/600 |
| 2004/0186358 A1* | 9/2004 | Chernow et al. ............ 600/300 |
| 2005/0024183 A1* | 2/2005 | Carter et al. ................ 340/5.61 |
| 2005/0035862 A1* | 2/2005 | Wildman et al. .......... 340/573.1 |
| 2005/0151640 A1* | 7/2005 | Hastings ................. 340/539.11 |
| 2007/0057057 A1* | 3/2007 | Andresky et al. ............. 235/451 |
| 2007/0085690 A1* | 4/2007 | Tran ......................... 340/573.1 |
| 2007/0120689 A1* | 5/2007 | Zerhusen et al. .......... 340/573.1 |
| 2007/0132597 A1* | 6/2007 | Rodgers ..................... 340/573.1 |
| 2007/0159332 A1* | 7/2007 | Koblasz .................... 340/572.1 |
| 2007/0163045 A1 | 7/2007 | Becker et al. |
| 2007/0174964 A1* | 8/2007 | Lemire et al. ..................... 5/600 |
| 2007/0268480 A1 | 11/2007 | Kaye |
| 2008/0001763 A1* | 1/2008 | Raja et al. ................. 340/573.1 |
| 2008/0004904 A1* | 1/2008 | Tran ................................. 705/2 |
| 2008/0126132 A1* | 5/2008 | Warner et al. ..................... 705/3 |
| 2009/0044334 A1* | 2/2009 | Parsell et al. ...................... 5/424 |
| 2009/0051545 A1* | 2/2009 | Koblasz .................... 340/573.1 |
| 2009/0063183 A1* | 3/2009 | McNeely et al. .................. 705/2 |
| 2009/0119843 A1* | 5/2009 | Rodgers et al. .................... 5/611 |
| 2009/0128344 A1* | 5/2009 | Sundaram et al. ......... 340/573.1 |
| 2009/0224924 A1* | 9/2009 | Thorp ....................... 340/573.1 |
| 2009/0231124 A1* | 9/2009 | Klabunde et al. ........ 340/539.12 |
| 2009/0267776 A1* | 10/2009 | Glenn et al. ............... 340/573.1 |
| 2010/0073162 A1 | 3/2010 | Johnson et al. |
| 2010/0117823 A1* | 5/2010 | Wholtjen ................. 340/539.13 |
| 2010/0117836 A1* | 5/2010 | Momen et al. ............ 340/573.1 |
| 2010/0321180 A1* | 12/2010 | Dempsey et al. ........ 340/539.12 |
| 2010/0328076 A1* | 12/2010 | Kyle et al. ................. 340/573.1 |
| 2011/0054936 A1* | 3/2011 | Cowan et al. ..................... 705/3 |
| 2011/0068930 A1 | 3/2011 | Wildman et al. |
| 2011/0144548 A1 | 6/2011 | Elliott et al. |
| 2011/0148586 A1* | 6/2011 | Anderson et al. ............ 340/10.1 |
| 2011/0193703 A1* | 8/2011 | Payton et al. ............. 340/573.1 |
| 2011/0247139 A1* | 10/2011 | Tallent et al. ...................... 5/613 |
| 2011/0254682 A1* | 10/2011 | Christensen ............ 340/539.12 |
| 2011/0291840 A1* | 12/2011 | Pelland et al. ............ 340/573.1 |
| 2011/0301440 A1* | 12/2011 | Riley et al. ................... 600/301 |
| 2012/0036636 A1* | 2/2012 | Stryker et al. ..................... 5/600 |
| 2012/0062382 A1* | 3/2012 | Taneff ....................... 340/573.1 |
| 2012/0072238 A1 | 3/2012 | Collins, Jr. et al. |
| 2012/0194338 A1* | 8/2012 | Snodgrass ................ 340/539.12 |
| 2012/0319835 A1* | 12/2012 | Schulmeister et al. .. 340/539.12 |
| 2012/0323591 A1* | 12/2012 | Bechtel et al. ..................... 705/2 |
| 2012/0323592 A1* | 12/2012 | Bechtel et al. ..................... 705/2 |
| 2013/0027199 A1* | 1/2013 | Bonner ................... 340/539.11 |
| 2013/0033376 A1* | 2/2013 | Momen et al. ........... 340/539.11 |
| 2013/0048705 A1* | 2/2013 | Tallent et al. .................. 235/375 |
| 2013/0253291 A1* | 9/2013 | Dixon et al. .................. 600/323 |
| 2013/0278399 A1* | 10/2013 | Graniewitz et al. ...... 340/286.06 |
| 2013/0293353 A1* | 11/2013 | McPherson et al. .......... 340/10.1 |
| 2013/0300572 A1* | 11/2013 | Mould-Millman et al. ........................ 340/870.01 |
| 2013/0342349 A1* | 12/2013 | Cruz ......................... 340/573.1 |
| 2014/0009292 A1* | 1/2014 | Long et al. ................. 340/573.1 |
| 2014/0049377 A1* | 2/2014 | Krusor et al. ................ 340/10.1 |
| 2014/0070950 A1* | 3/2014 | Snodgrass ................. 340/573.5 |
| 2014/0169795 A1* | 6/2014 | Clough ........................ 398/106 |

* cited by examiner

PATIENT SUPPORT APPARATUS WITH IN-ROOM DEVICE COMMUNICATION

CROSS-REFERENCE TO RELATED APPLICATION

This application claims the benefit of U.S. Pat. application Ser. 61/548,491, filed Oct. 18, 2011, entitled PATIENT SUPPORT APPARATUS WITH IN-ROOM DEVICE COMMUNICATION, which is incorporated by reference herein in its entirety.

BACKGROUND OF THE INVENTION

The present invention relates to a hospital communication system, and more particularly to a hospital communication system that includes a patient support apparatus—such as a bed, stretcher, cot, gurney, table, chair, or the like—that communicates with at least one other device positioned in the same room, or close to the same room. The other device may be a patient medical device, such as a respirator, ventilator, vital signs monitor, pump, or other type of patient medical device. Alternatively, or in addition, the other device may be a device intended for use by hospital personnel, such as a hand washing station or other type of device.

SUMMARY OF THE INVENTION

The system and methods of the present invention are adapted provide reminders and/or alerts to caregivers so that an improved quality of care may be provided to patients. Such alerts and/or reminders help to ensure that hospital personnel follow established patient care protocols and perform the various tasks associated with these protocols. Such protocols may include, but are not limited to, taking steps to: (1) reduce the likelihood and/or severity of a patient fall; (2) reduce the likelihood of a patient acquiring ventilator associated pneumonia; (3) ensure that a patient is turned with sufficient frequency to avoid the development of bed sores and/or for other reasons; and (4) ensure that hospital personnel and/or visitors wash their hands prior to approaching or touching a patient's bed.

According to one embodiment, a patient support system is provided that includes a patient support apparatus, a display, a wireless sensor, and a controller. The patient support apparatus includes a surface upon which a patient may be supported. The display may be supported on the patient support apparatus, or elsewhere, and displays status information about the patient support apparatus. The wireless sensor is positioned on the patient support apparatus and detects the presence of, and identity of, a mobile electronic tag positioned within the vicinity of the patient support apparatus. The controller communicates with the wireless sensor and the display, and the controller includes a memory in which a patient care protocol is stored. The patient care protocol applies to a patient who is assigned to the patient support apparatus. The controller determines if the patient care protocol is being implemented based upon the presence and identity of the mobile electronic tag. The controller further provides an indication on the display of any event which the patient care protocol indicates should be communicated to a caregiver.

According to another embodiment, a patient support system is provided that includes a patient support apparatus, a display, a wireless sensor, and a controller. The patient support apparatus includes a surface upon which a patient may be supported. The display is adapted to display status information about the patient support apparatus. The wireless sensor is positioned on the patient support apparatus and adapted to detect the presence of a mobile electronic tag worn by a caregiver. The wireless sensor also receives a wireless message from a hand washing station indicating whether the caregiver has washed his or her hands. The controller communicates with the wireless sensor and the display. The controller also determines when the mobile electronic tag approaches the patient support apparatus and issues an alert on the display if the caregiver approaches the patient support without having washed his or her hands at the hand washing station.

According to another aspect, a patient support system is provided that includes a patient support apparatus, a display that may be supported on the patient support apparatus or elsewhere, a wireless sensor positioned on the patient support apparatus, and a controller. The patient support apparatus includes a surface upon which a patient may be supported. The display displays status information about the patient support apparatus. The wireless sensor detects the presence of a mobile electronic tag attached to a piece of medical equipment used in the treatment of the patient. The controller communicates with the wireless sensor and the display, and is adapted to determine when the mobile electronic tag is positioned within a vicinity of the patient support apparatus. The controller also issues an alert on the display when the tag is positioned within the vicinity of the patient support apparatus wherein the alert reminds a caregiver of a specific configuration which the patient support apparatus should be in prior to the caregiver leaving a room in which the patient support apparatus is positioned.

According to yet another aspect, a patient support apparatus is provided that includes a base, a deck adapted to support a patient, a height adjustment mechanism, a visual indicator positioned on the patient support apparatus, a transceiver, and a controller. The height adjustment mechanism is adapted to adjust the height of the deck relative to the base. The transceiver communicates with an electronic device positioned within a common room in which said patient support apparatus is positioned. The electronic device is spaced apart from the patient support apparatus, and the transceiver is adapted to receive status information from the electronic device. The controller is supported on the patient support apparatus and is adapted to control the visual indicator in a manner that conveys the status information from the electronic device to a person located adjacent to the patient support apparatus.

According to other aspects of the invention, the mobile electronic tag may be attached to a caregiver, to a piece of medical equipment, to a hand washing station, to a patient, to a mattress, or to still other devices. The medical device may be a respirator, ventilator, pump, or other type of medical device. The wireless sensor may be configured to detect the presence of, and identity of, a plurality of mobile electronic tags that are simultaneously positioned within the vicinity of the patient support apparatus.

The patient care protocol may be determined based at least partially upon the identity and location of both the first and second mobile electronic tags. The patient care protocol may include maintaining a head of bed angle on the patient support apparatus above a predetermined angle in order to reduce the possibility of ventilator associated pneumonia occurring in a patient supported on the patient support apparatus. The patient care protocol may also, or alternatively, be determined based at least partially upon the identity and location of a mobile electronic tag worn by the patient.

Still further, the patient care protocol may be a fall prevention protocol and the event causing an alert to issue may include any failure to arrange the patient support apparatus in a fall prevention configuration. Such a fall prevention protocol configuration may include locking a brake on the patient support apparatus, raising siderails on the patient support apparatus, lowering the patient support apparatus, and/or turning on a bed exit alarm on the patient support apparatus.

The patient care protocol may also be determined by a database that correlates the identity of the tag to a specific patient.

The system may include, in some embodiments, at least three tags, a first of which is worn by a patient, at least a second of which is attached to a mobile medical device usable in the treatment of the patient, and at least a third of which is attached to a mattress positioned on the patient support surface. The system may further include a database correlating the mattress tag to at least one feature of the mattress.

The controller may be positioned on the patient support apparatus, or it may be positioned at a remote location, or it may be physically and/or logically distributed in a manner in which portions of it are located in different locations than other portions.

Any alerts and/or messages which are issued by the system may be transmitted to a remote location, such as a nurse's station, and/or they may be transmitted to a mobile device carried by the caregiver, such as, but not limited to, a smart phone, a cell phone, a pager, a personal digital assistant, a laptop, a Blackberry, or other mobile electronic device.

The display may be a liquid crystal display, a touch screen, a plasma screen, one or more lights, a speaker or audio-producing device, or any other type of screen, panel, or device that provides information to a user of the patient support apparatus. In some embodiments, the display may be positioned on the patient support apparatus, or it may be incorporated into a pendant that is attached to the patient support apparatus, or it may be located off of the patient support apparatus.

Before the embodiments of the invention are explained in greater detail, it is to be understood that the invention is not limited to the details of operation or to the details of construction and the arrangement of the components set forth in the following description or illustrated in the drawings. The invention may be implemented in various other embodiments and practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENT

Figure 1:
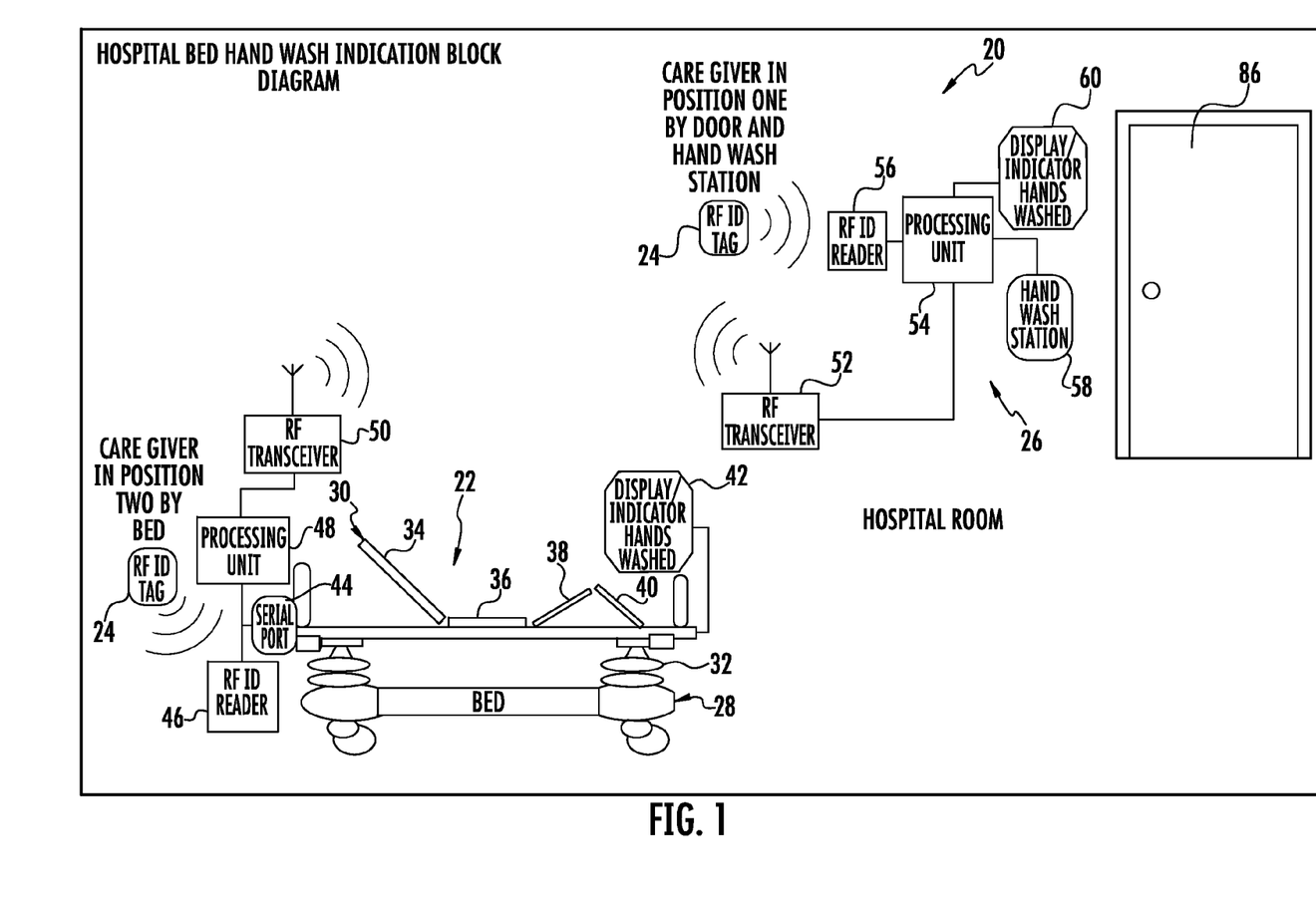
FIG. 1 is a diagram of a patient support system according to one embodiment.

A patient support system 20 according to one embodiment is shown in FIG. 1. Patient support system 20 includes a patient support apparatus 22, a mobile electronic tag 24, and a stationary electronic structure 26. The patient support apparatus 22 shown in FIG. 1 is a bed, but it will be understood that patient support apparatus 22 could be a stretcher, a cot, a gurney, a patient table, a chair, or any other structure used to support a patient in a health care setting. The mobile electronic tag 24 shown in FIG. 1 is a radio frequency tag, but it will be understood that other types of mobile electronic tags may be used. The stationary electronic structure 26 shown in FIG. 1 specifically includes a hand washing station 58 provided for people to clean their hands, although it will also be understood that the stationary electronic structure 26 could include other types of structures used by healthcare personnel and/or visitors.

In the embodiment shown in FIG. 1, patient support apparatus 22 includes a base 28, a deck 30, and a height adjustment mechanism 32 that raises and lowers the deck 30 relative to the base 28. Deck 30 in the embodiment shown is an articulating deck that includes a head section 34, a seat section 36, a thigh section 38, and a foot section 40. Other types of decks may be used with patient support system 20.

Patient support apparatus 22, in the embodiment illustrated, further includes a display 42 that is positioned at any suitable location on patient support apparatus 22. Display 42 can be a liquid crystal display, a plasma screen, one or more lights, one or more speakers, and/or any other structure capable of conveying information to a caregiver. Display 42 is configured to display one or more status conditions of patient support apparatus 22, such as whether the brake is set, whether the bed is in its lowest position, whether a bed exit alarm is set, and/or other information. In some embodiments, display 42 is incorporated into patient support apparatus 22, or it is incorporated into a pendant that is attachable to, and detachable from, patient support apparatus 22. In still other embodiments, display 42 may be positioned off of patient support apparatus 22.

Figure 2:
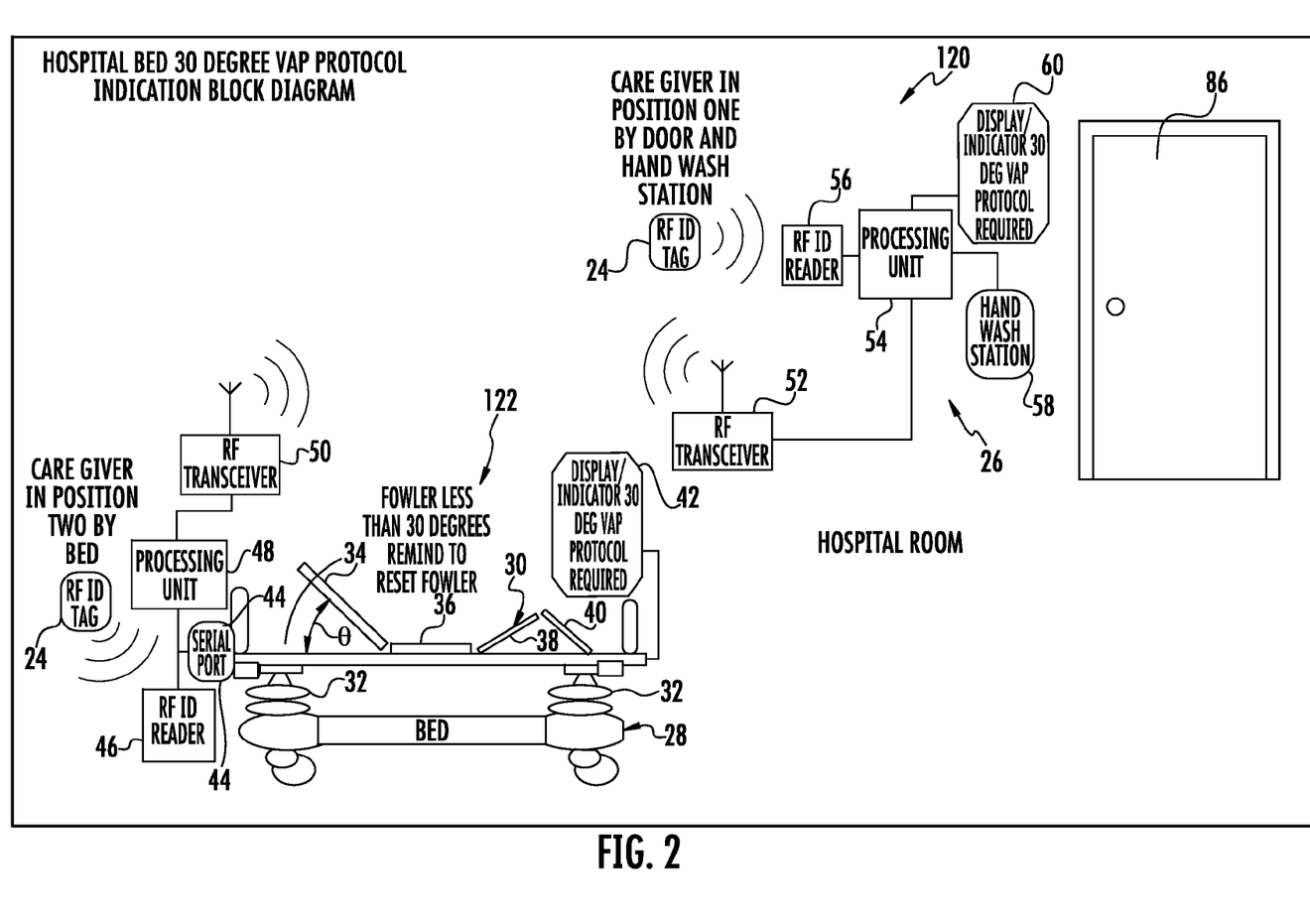
FIG. 2 is a diagram of another embodiment of the patient support system in which head of bed angle patient care protocol may be implemented by a caregiver or an electronic device controlled by a caregiver.
Figure 3:
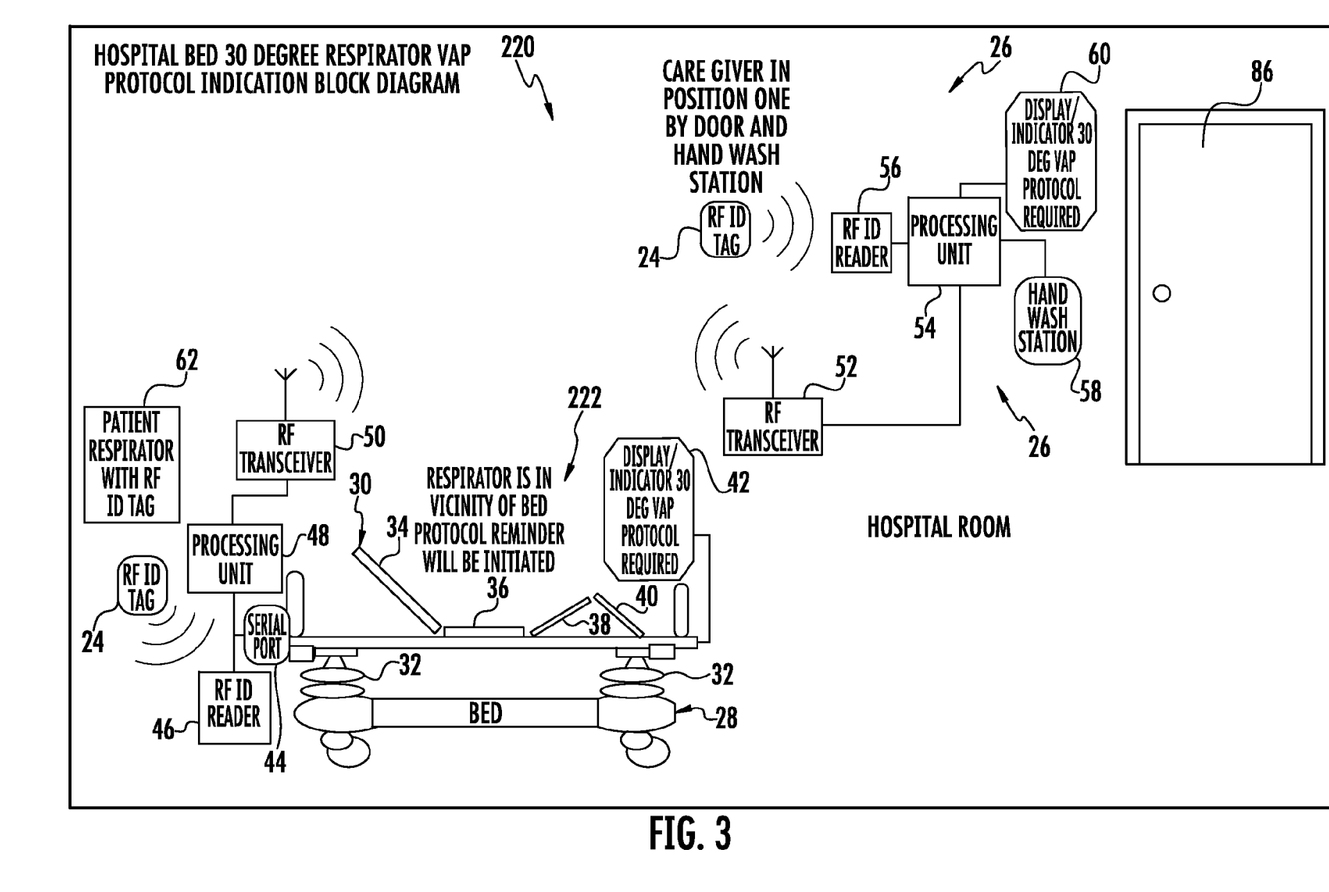
FIG. 3 is a diagram of yet another embodiment of the patient support system in which a head of bed angle patient care protocol may be implemented automatically by the detection of a medical device within the vicinity of a patient support apparatus.

Patient support apparatus 22 also further includes a serial port 44 to which is electrically coupled a wireless sensor 46, a processing unit 48, and an RF transceiver 50. These devices allow patient support apparatus 22 to communicate with stationary electronic structure 26 and the mobile electronic tags 24, as will be discussed more below. It will be understood by those skilled in the art that, while FIGS. 1-3 show a serial port 44 connection between support apparatus 22 and processing unit 48, other types of connections may be used. Such connections could be parallel connections, wireless connections, or other types of connections. Further, it will also be understood by those skilled in that art that—although FIGS. 1-3 show processing unit 48, transceiver 50, and tag reader 46 as being separate structures attached to, or supported on, patient support apparatus—these structures could be incorporated into the patient support apparatus 22 itself in some embodiments. When so incorporated, processing unit 48 may perform additional support apparatus functions beyond only those functions associated with transceiver 50 and reader 46.

Stationary electronic structure 26, in the embodiment of FIG. 1, includes an RF transceiver 52, a processing unit 54 in communication with RF transceiver 52, an electronic tag reader or RF ID reader 56, a hand washing station 58, and a display 60. Hand washing station 58 may be a commercially available hand washing station that includes appropriate sensors to determine if a person, such as a caregiver, has washed his or her hands or not. The determination of whether or not a person has washed their hands at station 58 can be accomplished in any known manner. In one manner, RF ID reader 56 detects the presence and identity of an RF ID tag 24 worn by the healthcare personnel when the tag 24 is positioned within the vicinity of station 58. This is accomplished through RF ID reader 56. Reader 56 passes this information onto processing unit 54, which may be any type of electronic structure capable or carrying out the processes described herein. To that end, processing unit 54 may include any one or more microprocessors, microcontrollers, integrated circuits, field programmable gate arrays, systems on a chip, volatile or nonvolatile memory, discrete circuitry, and/or other hardware, software, or firmware that carry out the functions described herein, as would be known to one of ordinary skill in the art.

Tags 24 and reader 56 (along with reader 46) may be commercially available tags and tag readers, or other types of tags and tag readers. Such tags may operate in any suitable RF ID frequency bands including, but not limited to, 120-150 kilohertz, 13.56 megahertz, 433 megahertz, 868-870 megahertz, 902-928 megahertz, 2450-5800 megahertz, and 3.10-10 gigahertz. Tag 24 include a unique number or other identifier associated with it which is read by reader 56. In one embodiment, tags 24 are be active tags that actively communicate with nearby readers. In another embodiment, tags 24 are passive tags that only transmit information in response to interrogations from one or more readers. In some embodiments, such passive RF ID tags 24 operate without the need for a battery or other independent power source. Instead, such tags utilize the power of the interrogating message to generate a responsive communication. Still other types of tags may also be used besides RF ID tags, such as, but not limited to infrared tags, or other types of position determining tags. Indeed, in one embodiment, one or more tags 24 include cards having magnetic stripes that are swiped through magnetic card readers.

Processing unit 54 is also in electrical communication with hand washing station 58. Hand washing station 58 is adapted to transmit a signal to processing unit 54 indicating if an individual has washed his or her hands. When such a signal is received by processing unit 54, processing unit 54 uses this signal to conclude that the individual associated with the specific RF ID tag 24 positioned adjacent station 58 has just washed his or her hands. Processing unit transmits the fact that this particular individual, or the person associated with a specific tag 24, has just washed his or her hands. This transmission is made via RF transceiver 52 and can include a time stamp, a date stamp, an indication of the specific hand washing station 58, an identification of the specific tag 24 associated with the person who washed his or her hands, and/or other information. The transmission is detected by RF transceiver 50 positioned on patient support apparatus 22, and processed in the manner discussed below.

Processing unit 54 of stationary electronic device 26 is further configured to determine if a person enters the hospital room, or other type of room, and does not wash his or her hands. In such cases, the hand wash station will not send a signal indicating a successful hand washing to processing unit 54. In such cases, the hand wash station may either omit sending any signals at all, or it may positively transmit a signal indicating the lack of a hand wash.

Processing unit 54 of stationary electronic device 26 will receive an indication from tag reader 56 when it detects the presence of a person within the vicinity of reader 56. Processing unit 54 will also receive a signal from tag reader 56 when that person exits the vicinity of tag reader 56. When processing unit 54 receives a signal from reader 56 indicating the presence of an individual, followed by a subsequent signal indicating the later departure of that individual—along with the absence of any signals indicating a hand wash from station 58—processing unit 54 concludes that an individual has entered the room and not utilized station 58 to wash his or her hands. In such a case, processing unit 54 transmits a signal through transceiver 52 indicating the lack of hand washing. This signal may include a time stamp, a date stamp, a specific number or other identifier that identifies the specific electronic tag 24 worn by the person who did not wash his or her hands, as well as other information.

When RF transceiver 50 receives a transmission from RF transceiver 52—whether indicating hand washing or the lack of hand washing—it passes that signal to processing unit 48, which, like processing unit 54, may include any electronic structures capable of performing the processes described herein, as would be known to one of ordinary skill in the art. Processing unit 48 is in electrical communication with tag reader 46 and serial port 44. Through serial port 44, processing unit 48 is capable of communication with additional electronics positioned on the bed (not shown). Both RF tag readers 46 and 56 are designed to only be able to detect tags 24 when they are positioned within close proximity to the respective tag readers 46 and 56, such as within several feet. In one embodiment, tag readers 46 and 56 use Zigbee communication protocols, or other radio based communications based on the IEEE 802 standard. Still other communication protocols may also be used, including, but not limited to, near field communication protocols.

The communication that takes place between tags 24 and any of readers 46 and/or 56, in one embodiment, utilizes a specific protocol and/or frequency (or set of frequencies) that differ from the protocol and/or frequencies used for the communication between transceivers 50 and 52. The communication between transceiver 50 and 52 can take on any suitable form for communicating over the typical distances one would expect in a health care facility. In at least one embodiment, transceivers 50 and 52 communicate directly with each other, while in at least another embodiment, transceivers 50 and 52 utilize one or more intermediary structures for such communication. One such intermediate structure might be health care computer network 72 (discussed in greater detail below). In such an embodiment, when transceiver 52 wishes to communicate with transceiver 50, it sends a message to the network 72 that is addressed to transceiver 52 and which is processed by an application on the network that then forwards the message to transceiver 50. Still other types of communication may be used.

When RF transceiver 50 receives the transmission from RF transceiver 52 indicating that an individual has washed his or her hands, RF transceiver passes that information to processing unit 48 for temporary storage in a memory (not shown) accessible to processing unit 48. Processing unit 48 later uses this information if the individual approaches patient support apparatus 22. The approach of the individual is detected by RF ID tag reader, which only senses tags 24 positioned within a defined range of patient support apparatus 22. This range is adjustable, in some embodiments. When processing unit 48 detects the presence of a tag 24 (via reader 46), it consults the memory in which messages from RF transceiver 50 are stored. These messages indicate whether the person associated with the specific tag 24 that has been detected has washed his or her hands or not. If the stored message indicates that the person has washed his or her hands, then processing unit 48 may take no action. Alternatively, processing unit 48 provides an indication to display 42, or to some other display or device, indicating that it has determined that the caregiver's hands have been washed.

If the stored message indicates that the person has not washed his or her hands, then processing unit 48 is programmed to issue an alert. Such an alert may take on any suitable form. In one embodiment, the alert includes displaying information on the display 42 that reminds the caregiver to wash his or her hands. In some embodiments, the displayed information includes flashing or colored messages. In other embodiments, more than one display 42 are positioned on the bed, and the alert involves displaying information on all of the available displays on patient support apparatus 22. Lights can also be positioned in areas separate from the displays 42, and such lights may be triggered as part of the alert indication. The alert may also, or alternatively, involve an audible signal, such as a beep, a voice message, or other audible signal, that is intended to prompt the caregiver to wash his or her hands. In still other embodiments, the alert may involve a combination of both visual and audible indications.

The message stored in the memory accessible to processing unit 48 that indicates a person has not washed his or her hands is based upon either an explicit message transmitted from stationary electronic structure 26, or it is based upon the absence of any positive signals transmitted from stationary electronic structure 26. That is, in the absence of receiving information indicating that a caregiver has washed his or her hands, processing unit 48 concludes that the caregiver has not washed his or her hands, and therefore issues an alert whenever such person approaches patient support apparatus 22.

In consulting the message information stored within memory, processing unit 48, in some embodiments, looks at the time stamp of the message stored within the memory. If the time stamp differs significantly from the current time, then processing unit 48 concludes that the hand washing did not occur during the latest visit by the health care worker to this particular room. In such cases, an alert of non-washed hands is initiated by processing unit 48. The amount of time difference between the present time and the time of hand washing necessary to trigger an alert is configurable, but may be on the order of a minute or two. Alternatively, or in addition, the decision on whether to issue a hand washing alert at patient support apparatus 22 can be based upon a determination that a particular caregiver has left the room subsequent to washing his or her hands at hand washing station 58. Any departure of the caregiver from the room may require a re-washing of his or her hands upon re-entry into the room in order to avoid generating a hand washing alert at the bed if the caregiver subsequently approaches the bed.

The determination that a particular caregiver has left the room is made by RF ID reader 56, either alone or in combination with other RF ID readers, such as RF ID reader 46. In one embodiment, such a determination is based upon the electronic tag 56 moving outside the detection range of either or both of these RF ID readers. Alternatively, other RF ID readers may be positioned in other locations within the health care facility and such RF ID readers may share information with each other through wireless communication. The determination that a health care worker has exited a particular room can therefore be based upon information received from another RF ID reader indicating the presence of that particular individual's tag 24 in a different location of the health care facility. The communication between the various RF ID readers occurs either through direct transmissions between the various RF ID readers, or via connection to a common computer network, such as a health care local area network 72 (discussed below), or it may occur by other means.

Processing unit 48, in some embodiments, is configured to transmit a request to stationary electronic structure 26 for status information about an individual if its memory does not contain any hand washing information about a particular individual. That is, if RF ID reader 46 detects the presence of a particular individual, and processing unit 48 cannot find in its memory any up-to-date status information about the cleanliness of that individual's hands, then processing unit 48 transmits a request for such information to either processing unit 54 of hand washing station 58, or to another remote structure that stores such information (such as hospital network 72, or more particularly to a specific server on the hospital network, that may be configured to receive and store all of the hand washing information from each of the stations 58 within a given facility).

In any of the embodiments discussed herein where hand washing station 58 communicates with the patient support apparatus, the monitoring of hand washing can be turned on automatically by the patient support apparatus upon the detection of a responsive transceiver (such as transceiver 52) associated with a hand washing station. Once turned on, support apparatus issues alerts any time a caregiver approaches without washing his or her hands. In an alternative embodiment, support apparatus includes a switch that must be activated in order to turn on the hand washing alerting feature. In some embodiments, the switch is implemented in hardware, while in other embodiments it is implemented in software. Regardless of how it is implemented, in some additional embodiments, a key is required so that only authorized individuals can turn this alerting feature off. Such a key may be implemented in either hardware or software. When implemented in software, a code, password, or the like is required to be entered into a keypad—or other user interface—on patient support apparatus 22 in order to turn the hand washing monitoring feature on or off. By limiting access to the controls for this feature to only authorized personnel, individual caregivers will not be able to simply disable the hand washing monitoring in order to circumvent the reminders and/or alerts that issue when they do not properly wash their hands.

FIG. 2 illustrates another embodiment of a patient support system 120 in which a patient care protocol designed to reduce the likelihood of a patient developing ventilator associated pneumonia (VAP) is built into a patient support apparatus 122. While the embodiment shown in FIG. 2 includes hand washing station 58 and its associated electronics, it will be understood by those skilled in the art that the embodiment of FIG. 2 can be constructed either with or without hand washing station 58. That is, in some embodiments, patient support system 120 need not have any interaction with any hand washing station. However, in other embodiments, patient support system 120 may communicate with a hand washing station in addition to monitoring one or more patient care protocols and issuing reminders and/or alerts regarding those patient care protocols, such as, but not limited to, patient care protocols relating to ventilator associate pneumonia (VAP).

The same reference numbers used to describe components of patient support system 20 will be used to describe patient support system 120 where the components function in the same manner as has been described. Components that are new to support system 120 will be given a new number. Components that are similar, but have been modified in a manner to be described, will be given the same reference number increased by one hundred. Thus, for example, the patient support apparatus of system 120 has been given the reference number 122 to signify that it is configured differently from patient support apparatus 22 of system 20. More specifically, and as will be described in more detail below, patient support apparatus 122, unlike patient support apparatus 22, includes programming and/or other configuration that allows a caregiver to implement a pneumonia prevention protocol.

One method of reducing the likelihood of ventilator associated pneumonia occurring in a patient is to ensure that the patient's torso does not lie flat. This can be accomplished by ensuring that head section 34 of patient support apparatus 122 does not get pivoted below a certain defined minimum angle (measured with respect to horizontal). Patient support system 120 is configurable to help ensure that this protocol is followed. Specifically, patient support apparatus 122 includes one or more sensors (not shown) that measure the current angular orientation of the head section 34 of deck 30. This angle is identified as angle θ in FIG. 2. The patient care protocol designed to reduce the likelihood of VAP will typically call for maintaining angle θ at or above a minimum angle, such as 30 degrees (although other angles may also be used).

Patient support system 120 is configured to help ensure compliance with this VAP reducing patient care protocol by detecting the close proximity of a patient caregiver to patient support apparatus 122 (via the caregiver's tag 24 and RF ID reader 46 of patient support apparatus 122). When a caregiver is close to patient support apparatus, processing unit 48 (or another electronic structure on support apparatus 122) will provide an alert if the head of bed (HOB) angle θ falls below the desired minimum angle. Such an alert is communicated to the caregiver via display 42, by audible means, or in any other fashion.

As an alternative to such alerting, patient support apparatus 122 is configured, in some embodiments, to issue an alert only if the HOB angle θ falls below the desired minimum and the caregiver is not near the bed (or other type of patient support apparatus), or is nearing an exit from the room, or has, in fact, left the room. In such embodiments, any HOB alerts are cancelled while the caregiver is adjacent the bed 122, thereby enabling the caregiver to move the patient and patient support 122 in any desired manner without triggering an unwanted alert. Only if the caregiver begins to leave the bed, or does in fact leave the bed, without configuring the bed with the desired HOB angle θ, will an alert be issued.

The determination that a caregiver is leaving the bed or room is made either via RF ID reader 46 alone, or in combination with one or more additional RF ID readers, such as RF ID reader 56 and/or other RF ID readers positioned in the health care facility. In one embodiment, RF ID reader 46 is adapted to determine a relative distance of the tag 24 to support apparatus 22, and when this relative distance is determined to be increasing, processing unit 48 issues an alert if the HOB angle is not at its desired minimum. In other embodiments, if RF ID reader 56 is positioned closer to the room's exit (such as doorway 86), the HOB angle alert may not be issued until RF ID reader detects the presence of the caregiver's tag 24, in which case RF ID reader 56 would communicate this information to processing unit 48 via transceivers 52 and 50. Other methods for determining the exit, or potential exit, of a caregiver may also be used.

Figure 4:
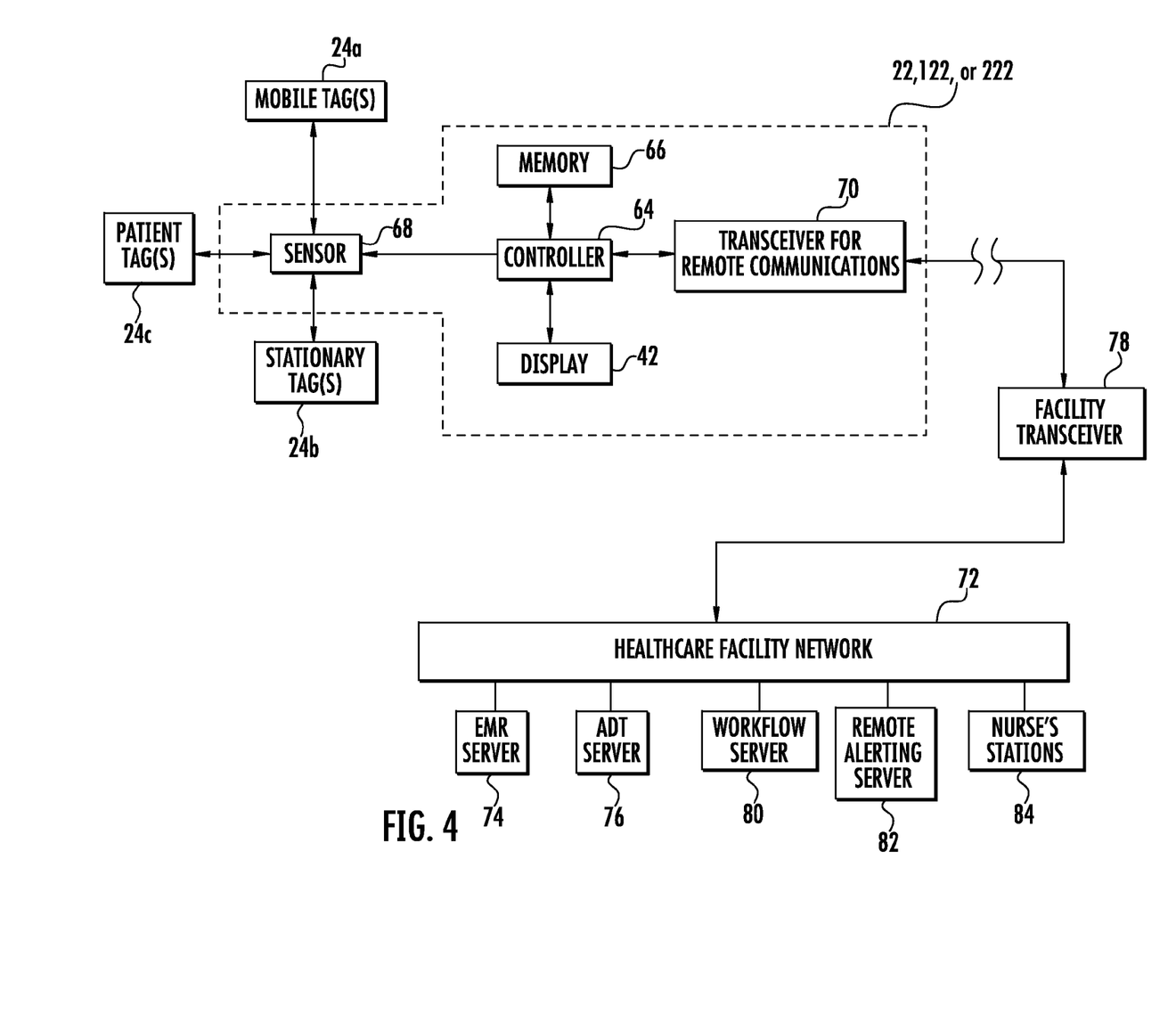
FIG. 4 is a block diagram of various elements of the patient support system that may be included in any of the embodiments depicted in FIGS. 1-3.

In another alternative embodiment, if a patient support apparatus 122 already has a protocol reminder function built into it for HOB angle alerts, patient support system 120 issues a reminder to a caregiver to turn on this alerting feature. This reminder may be accomplished automatically through data retrieved by patient support apparatus 122 from a health care computer network, such as network 72 (FIG. 4). Such data includes patient identification data and information contained with an electronic medical record, and/or any other information that enables a determination to be made that the HOB protocol should be implemented for the particular patient assigned to a particular patient support apparatus 122. When processing unit 48 determines that the HOB angle alert should be activated, and it also detects the presence of a nearby caregiver, it issues an alert on display 42, or through other means, to remind the caregiver that this alerting feature should be activated on the patient support apparatus 122. Such activation involves pressing one or more buttons, or taking other steps. Once activated, the bed (patient support apparatus 122) will issue an alert if it detects that the HOB angle has decreased below the desired threshold angle and no caregiver is present.

In any of the embodiments discussed herein, the alert that is generated when the patient support apparatus 122 is left with an undesirable HOB angle can take on a variety of forms. Because any alerts presented on display 42, or other displays on support apparatus 22, may not be seen by a caregiver leaving the room, it may be desirable to issue an audible alert. It may also be desirable to have processing unit 48 transmit an alert that will be communicated to a mobile electronic device carried by the particular caregiver who has just exited, or who is just about to exit, the room. Such communication is carried out by processing unit 48 transmitting a wireless message to a nearby wireless access point of the hospital's computer network. The message includes information about the alert, as well as the specific identifier for the tag 24. A separate alerting server or application in communication with the hospital network (e.g. remote alerting server 82 of FIG. 4) then transmits a wireless message to that individual's mobile electronic device. The server or application may be a third party commercially available mobile communication server or application. The mobile electronic device may be a basic cell phone, an Internet-enabled cell phone, a tablet computer, a laptop, a pager, a Blackberry, an iPad, or any other electronic device capable of receiving wireless transmissions, either from a cell tower, a wireless connection to a computer network, or from other sources.

In the system shown in FIG. 2, depending upon the specific configuration of support apparatus 122, it may be necessary for a caregiver to input information into patient support apparatus 122 that activates the HOB patient care protocol. This can be done by pressing appropriate buttons, or manipulating icons on display 42, or by touching a touch screen on support apparatus 122, or by entering information remotely that is then communicated to apparatus 122, or by other means. Only when such activation is manually carried out will the alerting feature described above be implemented. Thus, while the system shown in FIG. 2 is designed to help ensure compliance with a HOB angle patient care protocol, it may still be up to one or more caregivers to activate this protocol before such alerts are issued. In other embodiments, the HOB patient care protocol is automatically turned on so that any caregiver error in activating this protocol is avoided. Such automatic implementation of the HOB patient care protocol can take on a variety of different forms.

In one embodiment, the HOB patient care protocol is activated automatically by patient support apparatus 122 based upon information received from a remote computer, such as a server in communication with a hospital network. Patient support apparatus 122 is adapted to communicate with a hospital's computer network 72 (FIG. 4) either through a wireless connection (which may involve RF transceiver 50 or a separate transceiver), or a wired connection to the hospital's network, or both. Regardless of the connection type, patient support apparatus 122 is configured to receive information from a hospital's admission, discharge, and transfer (ADT) computer system 76, or from an electronic medical record (EMR) server 74, or from another source, indicating that the particular patient assigned to that specific patient support apparatus 122 should not have the HOB angle fall below the lower angular limit θ. The receipt of such information causes processing unit 48, or another processing unit on support apparatus 122, to automatically turn on the HOB angle patient care protocol alerting system. Once turned on, support apparatus 122 issues alerts any time support apparatus 122 has a HOB angle less than θ and no caregiver is located in the vicinity of apparatus 122.

In automatically turning on the HOB patient care protocol alerting system, patient support apparatus 122 can be configured, in at least one embodiment, to rely upon detecting the presence of an electronic tag 24 worn by the particular patient who is assigned to support apparatus 122. That is, RF ID tag reader 46 detects a specific tag 24 worn by the patient who is supported on support 122. Support apparatus 122 then uses this information in conjunction with information received from the hospital's network to determine whether to turn on the HOB patient care protocol alerting system. The information received from the hospital's network provides information specific to a particular patient, along with information correlating that patient to a particular tag 24. Support apparatus 122 then utilizes that information to make an independent determination of whether or not the HOB patient care protocol should be implemented or not. Alternatively, support apparatus 122 can be configured to not implement the HOB patient care protocol unless specifically instructed to do so, either from another electronic device, or from a caregiver.

FIG. 3 illustrates another embodiment of patient support system 220 in which a patient care protocol is implemented or modified based upon the detection of a medical device 62 positioned within the vicinity of support apparatus 222. As with the embodiment of FIG. 2, the embodiment of FIG. 3 is shown with the presence of a hand washing station 58 that communicates with patient support apparatus 222, but this is for illustration purposes only. The embodiment of FIG. 3 may be implemented either with or without the ability to communicate with hand washing station 58 (via transceiver 52).

Still further, as with the embodiment of FIG. 2, the same reference numbers used to describe components of patient support system 20 will be used to describe patient support system 220 where the components function in the same manner as has been described. Components that are new to support system 220 will be given a new number. Components that are similar, but have been modified in a manner to be described, will be given the same reference number increased by two hundred. Thus, for example, the patient support apparatus of system 220 has been given the reference number 222 to signify that it is configured differently from patient support apparatus 22 of system 20 and patient support apparatus 122 of system 120. More specifically, and as will be described in more detail below, patient support apparatus 222, unlike patient support apparatuses 22 and/or 122, includes programming and/or other configuration that allows it to automatically implement, or automatically suggest to a caregiver the implementation of, one or more different protocols, such as, but not limited to, the pneumonia prevention protocol discussed above. Thus, patient support apparatus 222 is configured with sufficient intelligence and sensor(s) to automatically recognize situations where a patient care protocol may be warranted, and then to either implement that protocol automatically, or to prompt a caregiver to decide whether to implement such a protocol.

In generally, patient support apparatus 222 recognizes the appropriateness of a specific patient care protocol based upon the detection, within a close proximity, of one or more specific medical devices 62. Depending upon the specific type of medical device 62, different protocols may be automatically implemented or suggested to the caregiver. Support apparatus 222 includes sufficient information, or has access to sufficient information, to identify what type of device medical device 62 is and determine the appropriateness of one or more protocols based upon the identification of the specific type of medical device. In some embodiments, this determination is made in conjunction with information support apparatus 222 obtains about the specific patient supported thereon, while in other embodiments, the protocol is chosen based solely upon the identification of the nearby medical device 62.

The specific medical device 62 illustrated in the embodiment of FIG. 3 is a respirator, although it will be understood by those skilled in the art that device 62 can take on other forms, such as, but not limited to, a ventilator, a pump, a monitor, or still other medical devices. As shown in FIG. 3, medical device 62 has an ID tag 24 attached to it that is detectable by RF ID reader 46. When ID reader 46 detects the presence of medical device 62, processing unit 48 determines the specific type of medical device that medical device 62 is. This determination is made by information stored on support apparatus 222 that correlates specific tags 24 to specific devices, or it is made by consulting similar information stored in one or more memories that are electronically accessible to support apparatus 222 by way of the hospital computer network 72. Regardless of the specific manner in which patient support apparatus 222 determines what type of medical device is adjacent to it, processing unit 48 is configured to change or implement a patient care protocol in response to the detection of that particular type of medical device. For example, it is common for the HOB angle patient care protocol to be desirably implemented when a patient is connected to a respirator. Therefore, patient support apparatus 222 is configured to automatically turn on the HOB angle patient care protocol alerting feature whenever it detects the presence of a respirator. Once turned on, patient support apparatus 222 will issue an alert in the manner described above any time the HOB angle falls below the minimum threshold and no caregiver is positioned within the vicinity of the support apparatus 222, as described above. By turning on this feature automatically any time a respirator is positioned adjacent support apparatus 222, it is not necessary for caregivers to manually turn this feature on, thereby reducing the potential for mistakenly overlooking this protocol, and potentially leaving a patient connected to a respirator at an undesired HOB angle.

In some embodiments, similar types of automatic implementation of HOB angle alerting are issued upon the detection of other medical devices within the vicinity of patient support apparatus 222, such as, but not limited to, ventilators. In additional embodiments, other types of patient care protocols are automatically implemented by patient support apparatus 222 based upon the detection of other types of medical devices 62 within the vicinity of support apparatus 222.

Any of patient support systems 20, 120, and/or 220 may also be used to help ensure compliance with a fall prevention patient care protocol. Such a fall prevention protocol is designed to help reduce the likelihood and/or severity of a fall by the specific patient assigned to patient support apparatus 22, 122, or 222. Such a protocol will typically involve configuring support apparatus 22, 122, or 222 in a specific manner designed to reduce the likelihood and/or severity of any falls. For example, one such protocol will require that any one or more of the following are implemented on the patient support apparatus: the height of the bed be changed to its lowest position, that at least the head end siderails are moved to their raised position, that the brake on the bed is set, and/or that a bed exit alerting system on the bed is activated. Patient support apparatus 22, 122, or 222 may be configured to automatically issue an alert if it determines that a caregiver has left, or is about to leave, the vicinity of the patient support apparatus without configuring support apparatus to meet one or more of these criteria. Thus, for example, if a caregiver leaves support apparatus 22, 122, or 222 without turning on the bed exit alerting system, support apparatus 22, 122, or 222 will issue an alert. Such an alert can be issued in a similar manner to that discussed for a HOB angle alert.

Just as with the HOB angle patient care protocol, patient support apparatus 222 is also configured, in some embodiments, but not so configured in still other embodiments, to automatically turn on the alerting system for the fall prevention patient care protocol. Further, just as with the HOB angle patient care protocol, this automatic activation may be based upon direct instructions from a remote location (such as via the hospital network 72), or it may be the result of a determination performed locally by processing unit 48. Such local processing can involve detecting an electronic tag 24 worn by the patient supported on support apparatus 222 and then determining if that particular patient corresponding to that tag is considered a fall risk by the health care facility. This determination is carried out by consulting one or more databases accessible to the support apparatus 222, such as databases that are in communication with the hospital's local area network 72, or other network that the support apparatus 222 has access to. Such databases will typically be accessible through EMR server 74 and/or ADT server 76. If the patient is considered a fall risk, then patient support apparatus 222 turns on the fall prevention protocol automatically and issues an alert if the support apparatus 222 is ever left unattended in a configuration that is not desirable for preventing, and/or reducing the severity of, any patient falls.

In addition to HOB angle and fall prevent protocols, patient support systems 20, 120, or 220 may also help to ensure compliance with one or more patient turning protocols. Such patient turning protocols are typically implemented in order to reduce the likelihood of a patient developing bed sores while supported on support apparatus 22, 122, or 222. When a turning patient care protocol is implemented, patient support apparatus 22, 122, or 222 is configured to issue an alert if a caregiver enters a room and leaves without performing a desired turn of the patient. The detection of the caregiver and his or her exit is carried out in the manner described above, or in other manners. The detection of a patient turn, or lack of a patient turn, is carried out—in one embodiment—via communication with a mattress (not shown) positioned on support apparatus 22, 122, or 222 that includes inflatable bladders, or other structures, that are used to turn a patient. Alternatively, the detection of a patient turn, or the absence of a patient turn, is carried out via communication with a pressure sensing sheet (not shown), or other types of sensors that monitor the position and/or orientation of a patient on support apparatus 22, 122, or 222. Examples of such pressure sensing sheets are disclosed in several commonly assigned, copending U.S. patent applications, including Ser. No. 61/546,546 filed Oct. 12, 2011 and entitled PRESSURE SENSING MAT; and Ser. No. 61/449,182 filed Mar. 4, 2011 and entitled SENSING SYSTEM FOR PATIENT SUPPORTS, the disclosures of which are both incorporated by reference herein in their entirety. Such communication with these structures is carried out by a direct wired connection to support apparatus 22, 122, or 222, or by wireless communication between these devices and support apparatus 22, 122, or 222.

As with the HOB angle and fall prevention protocols, the turning protocol is switched on automatically in some embodiments by the support apparatus based upon information specific to the particular patient being supported on the patient support apparatus. Again, the identity of the specific patient is determined based upon an electronic tag 24 worn by the patient, or by information communicated to the bed that indicates the identity of the patient. If the health care facility has designed this patient as one who should be turned with a particular minimum frequency, the patient support apparatus 22, 122, or 222 will issue an alert if a caregiver enters the room and subsequently leaves without turning the patient (when such a turning is due, or soon-to-be due).

In determining whether to issue such an alert, consideration is given to the amount of time since the patient was last turned. That is, if the patient is not due to be turned again for a relatively lengthy amount of time, then any entry and exit of a caregiver into and out of the room without performing another patient turn will not trigger any alerts by patient support apparatus 22, 122, or 222. The specific amount of this time is configurable by the caregiver in some embodiments, or by authorized personnel of the care giving institution. Alerts may also be issued by the support apparatus if the time since the last patient turn exceeds a predetermined maximum, regardless of whether any caregiver has entered and exited a particular room. That is, alerts are issued whenever a patient should be turned, even if the caregiver is not in the particular room and/or has not entered that room since the last turn. Such alerts are communicated to a nurse's station, or to individual electronic devices carried by caregivers. The turning protocol implemented by patient support apparatus 22, 122, or 222 may therefore not only help prevent a caregiver from forgetting to turn a patient while the caregiver is in the patient's room, but also help to ensure that a caregiver does not forget to enter the room with sufficient frequency to perform the desired patient turns.

In addition to the HOB angle, fall prevention, and turning patient care protocols, patient support systems 20, 120, and/or 220 can be configured, in some embodiments, to help ensure compliance with still other patient care protocols. One such additional patient care protocol is a dialysis protocol that attempts to limit movement of the patient during and/or immediately after a dialysis treatment. In one embodiment, a dialysis patient care protocol is automatically turned on when patient support apparatus 22, 122, or 222 detects the presence of a nearby dialysis machine that is carrying an electronic tag 24 (wherein the tag 24 contains sufficient information for the support apparatus to identify the machine as a dialysis machine. Alternatively, in another embodiment, a reminder to implement such a patient care protocol is issued to the caregiver when the nearby presence of a dialysis machine is detected, and the activation of the dialysis protocol is left to the manual intervention of the caregiver. The decision to automatically turn on the dialysis protocol or to issue a reminder to the caregiver to turn the protocol on is based on—in addition to the presence of the dialysis machine— information about the specific patient assigned to patient support apparatus 22, 122, or 222. More specifically, patient support apparatus 22, 122, or 222 consults an EMR server 74 or ADT server 76, or some other device, to determine if the patient supported thereon is a dialysis patient. Only if the patient is a dialysis patient, and the nearby presence of dialysis equipment is detected, will the support apparatus then turn on the dialysis monitoring protocol, or issue a reminder to the caregiver to activate this protocol.

In one embodiment, the dialysis patient care protocol issues an alert if the patient attempts to move, or does in fact move, out of the patient support apparatus 22, 122, or 222 while dialysis is occurring, or within a specific time period after the dialysis treatment is finished. In some cases, as will be discussed more below, the patient support apparatus 22, 122, or 222 is a chair, in which case the chair may include an exit detection system that detects when a patient is about to leave, or does in fact leave, the chair. Any detected patient movement or motion suggestive of an intent to leave will trigger an alert that, in some embodiments, is communicated remotely to alerting server 82 for forwarding onto the appropriate caregivers. Such alerts based upon patient movement may continue automatically for a predetermined time from the start of the dialysis treatment, or from the end of the dialysis treatment, in some embodiments. In other embodiments, the alerts continue until a caregiver disables the alerting feature manually. The dialysis alerts may be implemented in the same way as any of the previous alerts. That is, they may involve local visual and/or audio signals generated in one or more locations within the room, and/or they may involve the transmission of alert information to one or more remote locations, such as, but not limited to, remote alerting server 82.

In addition to the HOB angle, fall prevention, turning, and dialysis patient care protocols, patient support systems 20, 120, and/or 220 may be configured to help ensure compliance with still other patient care protocols. Such compliance is encouraged through the use of alerts and/or reminders issued by support apparatus 22, 122, or 222, along with the detection of the presence of a caregiver positioned by the support apparatus 22, 122, or 222. If the caregiver leaves without performing a desired task, an alert or a reminder is issued. Still further, as has been discussed, support apparatus 22, 122, or 222 will include the intelligence to automatically determine what those desired tasks are based upon any one or more of the following: the identity of the patient assigned to the support apparatus, the presence of one or more medical devices 62 adjacent the support apparatus, and information received from one or more electronic devices and/or applications that are in communication with the support apparatus (such as EMRs, the healthcare facility's ADT system, information input at the nurse's station, and other sources). Patient support apparatus 22, 122, or 222 may therefore automatically correlate patients and/or medical equipment with specific protocols and automatically turn on—or automatically remind a caregiver to manually turn on—alerting features associated with those patient care protocols to help ensure caregivers comply with those protocols.

FIG. 4 illustrates in block diagram format one embodiment of the basic electronic structures that can be used in any of the patient support systems 20, 120, and 220. As shown therein, the patient support apparatus 22, 122, or 222 includes a controller 64 that is in electrical communication with a memory 66, a display 42, a sensor 68, and a transceiver 70 for communicating with remote structures. Controller 64 may be the same as processing unit 48 or it may include processing unit 48 along with additional processing structures, such as one or more structures used to control movement and/or settings of the patient support apparatus 22, 122, or 222. Controller 64 may include one or more microprocessors, microcontrollers, integrated circuits, field programmable gate arrays, systems on a chip, volatile or nonvolatile memory, discrete circuitry, and/or other hardware, software, or firmware that carry out the functions described herein, as would be known to one of ordinary skill in the art.

Memory 66 may be any memory that stores information necessary to carry out the functions and algorithms described herein. Such memory may be volatile or non-volatile. Such memory may be used for storing messages transmitted by hand washing station 58, as well as any information received from other electronic devices, such as, but not limited to, information received from healthcare facility network 72.

Controller 64 is further in communication with a sensor 68 that is adapted to detect various electronic tags 24. Sensor 68 may be the same as RF ID reader 46, or it may use other types of sensing technology besides radio frequency detection. As shown in FIG. 4, sensor 68 detects mobile tags 24a (such as those worn by caregivers or attached to mobile medical devices), stationary tags 24b, (such as those attached to stationary structures in the healthcare facility), and/or patient tags 24c. Sensor 68 is adapted, in at least one embodiment, to not only detect the presence of these tags, but to also read specific identity information associated with the tags so that either the unique tag, or a unique type of tag, can be discerned by controller 64. In determining the identity of a tag, or the personnel and/or equipment associated with the tag, controller 64 consults a look-up table stored in memory 66, or it communicates with remote devices via transceiver 70.

Remote transceiver 70 allows patient support apparatus 22, 122, or 222 to communicate with remote devices. Remote transceiver 70, in at least one embodiment, is the same as RF transceiver 50. Alternatively, remote transceiver 70 may be separate from RF transceiver 50, in which case support apparatus 22, 122, or 222 may include at least two transceivers for remote communications. Remote transceiver 70, in the illustrated embodiment, is adapted to allow support apparatus 22, 122, or 222 to communicate with an existing computer network 72 that is run by the health care facility in which support the support apparatus is located. This computer network 72 may be a local area network, a plurality of LANs connected together, a wide area network, or still other types of networks. Such a network typically exists in health care facilities for running the various electronic and data communication functions of the health care facility. Communication with the network 72 is accomplished through a facility transceiver 78, which may be a conventional wireless access point to the network 72 (e.g. WiFi), or it may be another type of transceiver. In some systems, network 72 will be in communication with the Internet to thereby allow patient support apparatus 22, 122, or 222 to access information from, and transmit information to, other Internet-coupled computers that may be located off of the premises of the health care facility.

Healthcare facility network 72 will typically include a number of different types of commercially available servers and/or computer applications, depending upon the particular health care facility in which the patient support apparatus is located. Such servers may include an electronic medical (EMR) server 74; an admission, discharge and transfer (ADT) server 76; a work flow server 80; a remote alerting server 82; and/or one or more nurse's stations 84. EMR server 74 may contain medical information about a particular patient that support apparatus 22, 122, or 222 accesses in order to determine whether to implement one or more of the patient care protocols discussed herein. ADT server will typically include information allowing support apparatus 22, 122, or 222 to determine which patient is presently occupying the support apparatus, and therefore to know which information is relevant in EMR server 74. Work flow server 80 contains information identifying health care personnel, including which caregivers are assigned to which patients. Support apparatus 22, 122, or 222 accesses this information in order to determine which caregivers should be notified of any alerts issued by the support apparatus. Remote alerting server 82 controls alerts that are issued to wireless devices carried by hospital personnel. Patient support apparatus 22, 122, or 222 sends alerts, in some embodiments, to server 82 for it to forward onto designed caregivers. Nurse's stations 84 may also be in communication with network 72 so that any alerts issued by the support apparatuses may be communicated to personnel at the facility's nurse's stations.

It will be understood by those skilled in the art that any of patient support systems 20, 120, and 220 in accordance with the disclosure herein can be constructed, in at least one embodiment, to only implement one of the alerting and/or reminder functions described herein. That is, for example, in one embodiment, system 20 may issue alerts and/or reminders only when a caregiver fails to wash his or her hands. In other embodiments, for example, system 120 may issue HOB angle alerts and/or reminders only when a ventilator is detected nearby. In still other embodiments, system 220 may issue only bed exit alerts and/or reminders. Still further, however, it will also be understood that the features of systems 20, 120, and 220 may be combined in any manner, including, but not limited to, any combination of two or more of the alerting and/or reminders discussed herein. Thus, systems 20, 120, and/or 220 may be implemented with any one or more types of alerts and/or reminders.

It will also be understood that, in at least some embodiments, more than one patient support apparatus 22, 122, or 222 may be present that is used, or potentially used, by a given patient. For example, in a hospital room, a patient may have a bed assigned to him or her, and one or more chairs may also be positioned in the room. In such situations, the chair, or other secondary patient support apparatus, may be in communication with the primary patient support apparatus (e.g. the bed). The chair may be equipped with an occupancy sensor that determines the presence of an individual in the chair. Such sensors may include load cells, electronic tags 24 and tag readers, or other types of sensors. The chair may further include a processing unit akin to processing unit 48, a transceiver that communicates with transceiver 50, and, in some cases, an RF ID tag reader that is capable of detecting tags 24. The chair may implement any of the alerts or reminders discussed above. Such alerts may be implemented on a display (or audio device) attached to the chair, or they may be implemented on other displays (or audio devices), and/or they may be implemented by sending communications to other devices. As one example, the chair may issue an alert or reminder to a caregiver if he or she approaches the chair while the chair is occupied and the health care worker has not washed his or her hands.

In one embodiment, the chair talks to the other patient support apparatus and issues alerts and/or reminders through, or on, the other patient support apparatus. Thus, for example, if a chair is implemented with a chair exit alerting system, the chair would be capable of issuing an alert that is then passed onto patient support apparatus 22, 122, or 222. The patient support apparatus 22, 122, or 22 is capable of then forwarding that alert onto network 72 to remote alerting server 82, which forwards the alert to specific caregivers. As another alternative, the patient support apparatus 22, 122, or 222 may display alerts (or issue audible alerts) received from the chair locally on display 42 (or an audio generating device) without transmitting them to remote locations.

The above description is that of various embodiments of the invention. Alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support system comprising:
   a patient support apparatus having a surface upon which a patient may be supported;
   a display supported on said patient support apparatus for displaying status information about the patient support apparatus;
   a wireless sensor positioned on said patient support apparatus and adapted to detect the presence of, and identity of, a plurality of mobile electronic tags that are simultaneously positioned within a vicinity of the patient support apparatus, a first one of said mobile electronic tags being attached to a patient assigned to the patient support apparatus and a second one of the mobile electronic tags being attached to a piece of medical equipment used in the treatment of the patient, the wireless sensor communicating directly with the first and second mobile electronic tags when the first and second mobile electronic tags are within the vicinity of the patient support apparatus; and
   a controller positioned on the patient support apparatus and in communication with the wireless sensor and the display, said controller including a memory in which a patient care protocol is stored, said patient care protocol applying to a patient assigned to said patient support apparatus and determined based at least partially upon the identity and location of both the first and second mobile electronic tags, said controller adapted to determine if the patient care protocol is being implemented based upon the presence of the first and second mobile electronic tags, and said controller further adapted to provide an indication on the display of any event which the patient care protocol indicates should be communicated to a caregiver.

2. The system of claim 1 further comprising:
   a patient fall prevention protocol stored in said memory, said patient fall prevention protocol applying to the patient assigned to said patient support apparatus, said controller adapted to determine if the patient fall prevention protocol is being implemented based upon the presence of a third mobile electronic tag worn by a caregiver and a failure of the caregiver to perform at least two of the following actions: locking a brake on the patient support apparatus, raising siderails on the patient support apparatus, lowering the patient support apparatus, and turning on an exit alarm on the patient support apparatus; and said controller further adapted to provide an alert if the caregiver fails to perform at least two of the actions.

3. The system of claim 2 wherein said controller is further adapted to generate a message relating to the alert for transmission to a remote location.

4. The system of claim 1 wherein the patient care protocol includes maintaining a head of bed angle on said patient support apparatus above a predetermined angle in order to reduce the possibility of ventilator associated pneumonia occurring in the patient supported on the patient support apparatus.

5. The system of claim 4
wherein said controller is further adapted to remind a caregiver to move a head portion of the patient support apparatus to an angle greater than said predetermined angle if the head portion of the patient support apparatus is less than the predetermined angle.

6. The system of claim 5 wherein said piece of medical equipment is a ventilator or respirator.

7. The system of claim 1 wherein said wireless sensor is further adapted to communicate over at least two different communication channels, a first communication channel enabling said wireless sensor to communicate with said mobile electronic tags and a second communication channel enabling said wireless sensor to communicate with a non-mobile device positioned within the vicinity of the patient support apparatus.

8. The system of claim 7 wherein said non-mobile device is a hand washing station adapted to wirelessly communicate status information indicating whether the caregiver has washed his or her hands, said controller being further adapted to provide a visual reminder on the patient support apparatus to the caregiver if the caregiver approaches the patient support apparatus without first having washed his or her hands at the hand washing station.

9. The system of claim 8 wherein said mobile electronic tag is worn by the caregiver and both said hand washing station and the wireless sensor of the patient support apparatus are able to detect the presence and identity of the mobile electronic tag.

10. The system of claim 1 wherein said wireless sensor is further adapted to detect the presence of, and identity of, a third mobile electronic tag attached to a mattress positioned on said surface.

11. The system of claim 1 wherein
the wireless sensor is further adapted to detect the presence of, and identity of, a third mobile electronic tag worn by a caregiver,
the patient care protocol includes configuring the patient support apparatus in a desired configuration, and the controller is adapted to issue an alert if the caregiver leaves the vicinity of the patient support apparatus without configuring the patient support apparatus in the desired configuration.

12. The system of claim 11 wherein the controller is further adapted to determine the desired configuration of the patient support apparatus based upon the detection of the first mobile electronic tag.

13. The system of claim 1 wherein said patient support apparatus is a bed.

14. The system of claim 1 further comprising:
a patient turning protocol stored in said memory, said patient turning protocol applying to the patient assigned to said patient support apparatus, said controller adapted to determine if the patient turning protocol is being implemented based upon the presence of the first mobile electronic tag and outputs from a turning sensor positioned on the patient support apparatus, and said controller further adapted to issue an alert if a caregiver enters a room in which the patient support apparatus is located and leaves without performing a patient turn in accordance with the patient turning protocol.

15. The patient support system of claim 14 wherein the turning sensor includes a mattress positioned on the patient support apparatus having an inflatable bladder.

* * * * *